US012734308B2

(12) United States Patent
Chae

(10) Patent No.: US 12,734,308 B2
(45) Date of Patent: Sep. 15, 2026

(54) MEDICAL NEEDLE UNIT WITH AIR FILTER PART FOR PREVENTING AIR INJECTION

(71) Applicant: THE CATHOLIC UNIVERSITY OF KOREA INDUSTRY-ACADEMIC COOPERATION FOUNDATION, Seoul (KR)

(72) Inventor: Min Suk Chae, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 636 days.

(21) Appl. No.: 18/347,713

(22) Filed: Jul. 6, 2023

(65) Prior Publication Data

US 2024/0042141 A1 Feb. 8, 2024

(30) Foreign Application Priority Data

Aug. 2, 2022 (KR) ........................ 10-2022-0095951

(51) Int. Cl.
*A61M 5/32* (2006.01)

(52) U.S. Cl.
CPC ..................... *A61M 5/3293* (2013.01); *A61M 2202/0028* (2013.01)

(58) Field of Classification Search
CPC ........ A61M 5/3293; A61M 2202/0028; A61M 5/38; A61M 5/162; A61M 5/165; A61M 5/385; A61M 2005/1655; A61M 2005/1657; A61M 2205/75; A61M 2205/7527; A61B 8/0833; A61B 8/5269
See application file for complete search history.

(56) References Cited

U.S. PATENT DOCUMENTS

| | | | | |
|---|---|---|---|---|
| 3,978,857 | A * | 9/1976 | McPhee ................ | A61M 5/165 604/257 |
| 4,137,917 | A * | 2/1979 | Cohen ................. | A61M 5/3145 604/513 |
| 4,675,017 | A * | 6/1987 | Sato ...................... | B29C 66/727 604/405 |
| 6,319,236 | B1 * | 11/2001 | Bock ...................... | B01D 35/00 604/905 |
| 7,611,504 | B1 * | 11/2009 | Faries, Jr. ........... | A61M 39/045 604/113 |
| 2006/0264834 | A1 * | 11/2006 | Vaillancourt ..... | A61M 39/0606 604/167.02 |
| 2012/0022449 | A1 * | 1/2012 | Kim ...................... | A61M 5/385 604/126 |

(Continued)

FOREIGN PATENT DOCUMENTS

| | | | | |
|---|---|---|---|---|
| AU | 2011217210 A1 | * 10/2012 | ............ | A61M 5/165 |
| CA | 2638018 C | * 11/2016 | ......... | A61B 17/3401 |

(Continued)

*Primary Examiner* — Cris L. Rodriguez

(74) *Attorney, Agent, or Firm* — Bridgeway IP Law Group, PLLC; Jihun Kim

(57) ABSTRACT

An embodiment provides a medical needle unit with an air filter part for preventing air injection, the medical needle unit being designed to prevent qualitative deterioration of ultrasound images due to unexpected air injection in ultrasound-guided procedure and operation environments.

14 Claims, 7 Drawing Sheets

(56) References Cited

U.S. PATENT DOCUMENTS

| | | | | |
|---|---|---|---|---|
| 2012/0029465 | A1 * | 2/2012 | Wu | A61M 5/34<br>604/533 |
| 2015/0080814 | A1 * | 3/2015 | Lambert | A61M 39/105<br>604/535 |
| 2015/0283032 | A1 * | 10/2015 | Lin | A61M 5/38<br>604/406 |
| 2016/0081878 | A1 * | 3/2016 | Marks | A61J 1/2082<br>604/414 |
| 2021/0100977 | A1 * | 4/2021 | Piferi | A61M 25/0097 |
| 2023/0091363 | A1 * | 3/2023 | Linkner | A61K 38/4893<br>604/416 |
| 2023/0364336 | A1 * | 11/2023 | Smith | A61M 5/16809 |
| 2024/0216664 | A1 * | 7/2024 | Gill | A61M 39/10 |

FOREIGN PATENT DOCUMENTS

| | | | | | |
|---|---|---|---|---|---|
| CN | 101884814 | A | * | 11/2010 | A61M 5/3145 |
| CN | 101378798 | B | * | 6/2012 | A61B 17/3401 |
| KR | 10-1508919 | B1 | | 4/2015 | |
| KR | 101819116 | B1 | * | 1/2018 | A61M 5/3293 |

* cited by examiner

MEDICAL NEEDLE UNIT WITH AIR FILTER PART FOR PREVENTING AIR INJECTION

BACKGROUND OF THE INVENTION

Field of the Invention

The present disclosure relates to a medical needle unit, in more detail, a medical needle unit with an air filter part for preventing air injection, the medical needle unit being designed to prevent qualitative deterioration of ultrasound images due to unexpected air injection in ultrasound-guided procedure and operation environments.

Description of the Related Art

The necessity of using ultrasound equipment in the processes of diagnosing and treating patients is dramatically increasing. Use of ultrasound increases accuracy in procedures or operations in addition to stability in noninvasive treatment and decreases the frequency of attempts of the procedures or operations, thereby being able to expect the effect of reducing costs.

Ultrasound guidance is generally used to locally anesthetize and reduce pain of patients in Anesthesiology and Pain medicine and is replacing the landmark guidance or nerve stimulator guidance of the related art.

However, unexpected injection of air causes qualitative deterioration of ultrasound images due to the characteristics of ultrasound and has a negative influence on stability and accuracy that are the representative characteristics of ultrasound-guided procedures or operations.

Accordingly, it is increasingly required to prevent unexpected air injection in ultrasound-guided procedures or operations.

CITATION LIST

Patent Literature

Patent Literature 1: Korean Patent No. 10-1508919 (published on Apr. 14, 2015)

SUMMARY OF THE INVENTION

The present disclosure has been made in an effort to solve the problems in the related art described above, and an objective of the present disclosure is to provide a medical needle unit with an air filter part for preventing air injection, the medical needle unit being designed to prevent qualitative deterioration of ultrasound images due to unexpected air injection in ultrasound-guided procedure and operation environments.

The objectives to implement in the present disclosure are not limited to the technical problems described above, and other objects that are not stated herein will be clearly understood by those skilled in the art from the following specifications.

In order to achieve the objectives described above, an embodiment of the present disclosure provides a medical needle unit with an air filter part for preventing air injection, including: an air filter part 10 having a built-in filter unit 100 for preventing air injection; a medical needle part 20 coupled to an end of the air filter part 10; and a medicine injection part 30 and 30' coupled to an end of the air filter part 10 opposite to the end to which the medical needle part 20 is coupled to couple an external medicine injector.

The air filter part 10 may include: a filter supporting tube 11 having a through-hole formed through a center axis therein; and the filter unit 100 disposed in the filter supporting tube 11.

The filter supporting 11 tube may include: a first air filter part coupler tube 12 that is an end facing the medical needle part 20 and is inserted in the medical needle part 20; and a second air filter part coupler tube 13 that is an end facing the medicine injection part 30 and 30' and is coupled to the medicine injection part 30 and 30'.

The first air filter part coupler tube 12 may have an outer diameter for insertion in a first medicine injection part coupler 312 of the medicine injection part 30 and 30', and an inner diameter for inserting a medicine injection tube 313 of the medicine injection part 30 and 30' into the first air filter part coupler tube 12.

The second air filter part coupler tube 13 may have an inner diameter for inserting a medical needle part coupler 22 of the medical needle part 20.

The air filter unit 100 may include: a first cover 110 having a medicine injection tube coupler tube 111 on a top thereof; an air injection preventing filter 120; a filter supporter 130; and a second cover 140 having a medicine discharge tube 141 on a bottom thereof, and the air injection preventing filter 120 and the filter supporter 130 may be sealed between the first cover 100 and the second cover 140.

The air injection preventing filter 120 may be manufactured to have apertures of 0.1 to 0.45 μm.

Any one of an outer diameter, a long radius, or a diagonal line of the air injection preventing filter 120 may be 4 to 50 mm.

The medical needle part 20 may include: a medical needle 29 that is inserted into an affected area for a ultrasound procedure or operation to inject a medicine for ultrasound treatment; and a medical needle holder 21 through which a second end of the medical needle 29 is inserted and fixed and that has a medical needle part coupler 22 coupled to a second air filter part coupler tube 13 of the air filter part 10.

The medical needle part coupler 22 may further include, on a surface facing the air filter part 10, a medicine discharge tube coupler 23 recessed and having an inner diameter corresponding to an outer diameter of a medicine discharge tube 141 of the air filter part 10 so that the medicine discharge tube 141 is inserted therein.

The medical needle part coupler 22 may be configured to detachably couple the medical needle holder 21 to the air filter part 10.

The medicine injection part 30 and 30' may include: an air filter part coupler 310 to which the air filter part 10 is coupled; and an external medicine injector coupler 320 extending from the air filter part coupler 310 to the medicine injection part 30 and 30' so that the external medicine injector is coupled.

The air filter part coupler 310 may include: a medicine injection part shell 311; and a medicine injection tube 313 formed in the medicine injection part shell 311 at a predetermined distance from an inner surface of the medicine injection part shell 311 to form a region of a first medicine injection part coupler 312.

Connection portions of the medicine injection part shell 311 and the external medicine injector coupler 320 of the medicine injection tube 313 may be integrally connected.

The medicine injection part may be configured such that the air filter part coupler 310 and the external medicine injector coupler 320 are separated, and may further include an extension tube 40 connecting the air filter part coupler 310 and the external medicine injector coupler 320.

In order to achieve the objectives described above, another embodiment of the present disclosure provides a medical needle unit with an air filter part for preventing air injection, including: an air filter part 10; a filter unit 100*a* coupled to the air filter part 10; a medicine injection part 30 and 30' coupled to an end of the filter unit 100*a* that is opposite to an end to which the air filter part 10 is coupled; and a medical needle part 20 coupled to the other end of the air filter part 10 that is different from the end to which the filter unit 100*a* is coupled.

DETAILED DESCRIPTION OF THE PREFERRED EMBODIMENTS

Figure 1:
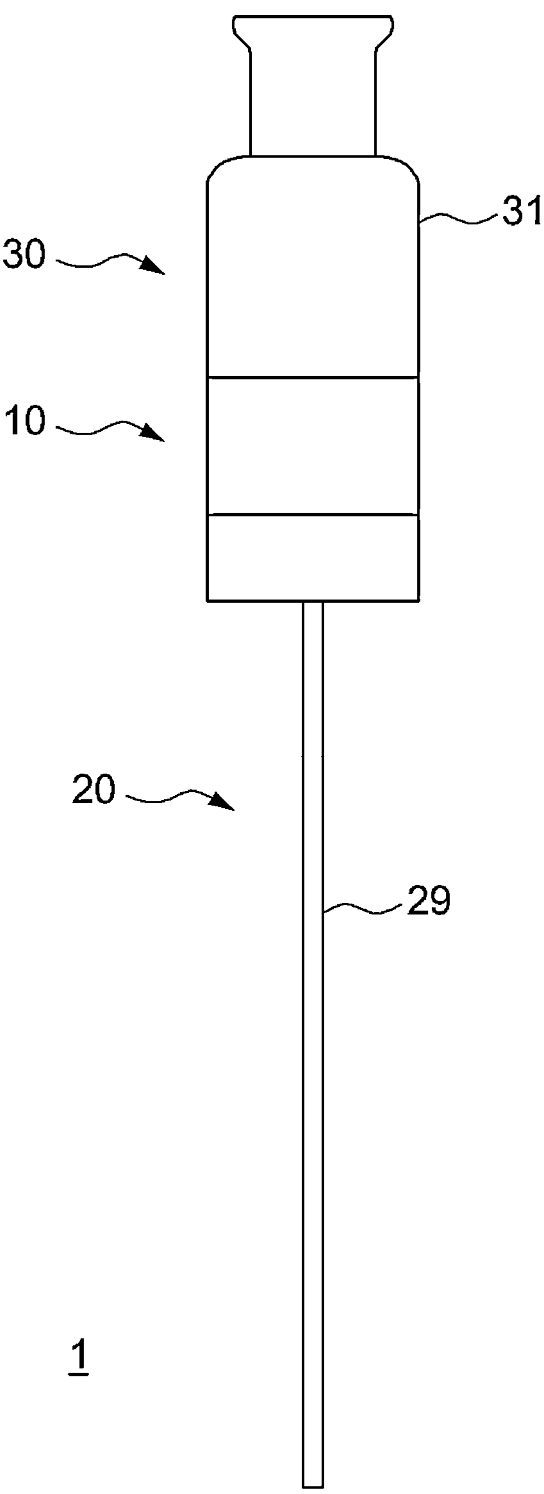
FIG. 1 is a side view of a medical needle unit 1 with an air filter part for preventing air injection according to an embodiment of the present disclosure.

In the following description of the present disclosure, detailed descriptions of well-known functions or configurations relating to the present disclosure will not be provided when it is determined that they may unnecessarily obscure the point of the present disclosure.

Embodiments described herein may be changed in various ways and may have various shapes, so specific embodiments are shown in the drawings and will be described in detail in this specification. However, it should be understood that the exemplary embodiments according to the concept of the present disclosure are not limited to the embodiments which will be described hereinbelow with reference to the accompanying drawings, but all of modifications, equivalents, and substitutions are included in the scope and spirit of the disclosure.

It is to be understood that when one element is referred to as being "connected to" or "coupled to" another element, it may be directly coupled or connected to another element or there may be another element interposed therebetween. On the other hand, it should be understood that when one element is referred to as being "connected directly to" or "coupled directly to" another element, it may be connected to or coupled to another element without the other element intervening therebetween. Further, the terms used herein to describe a relationship between elements, that is, "between", "directly between", "adjacent" or "directly adjacent" should be interpreted in the same manner as those described above.

Terms used in the present disclosure are used only to describe specific exemplary embodiments rather than limiting the present disclosure. Singular forms are intended to include plural forms unless the context clearly indicates otherwise. It will be further understood that the terms "comprise" or "have" used in this specification specify the presence of stated features, numerals, steps, operations, components, parts, or a combination thereof, but do not preclude the presence or addition of one or more other features, numerals, steps, operations, components, parts, or a combination thereof.

Hereafter, the present disclosure is described in detail with reference to the accompanying drawings showing an embodiment of the present disclosure.

Figure 2:
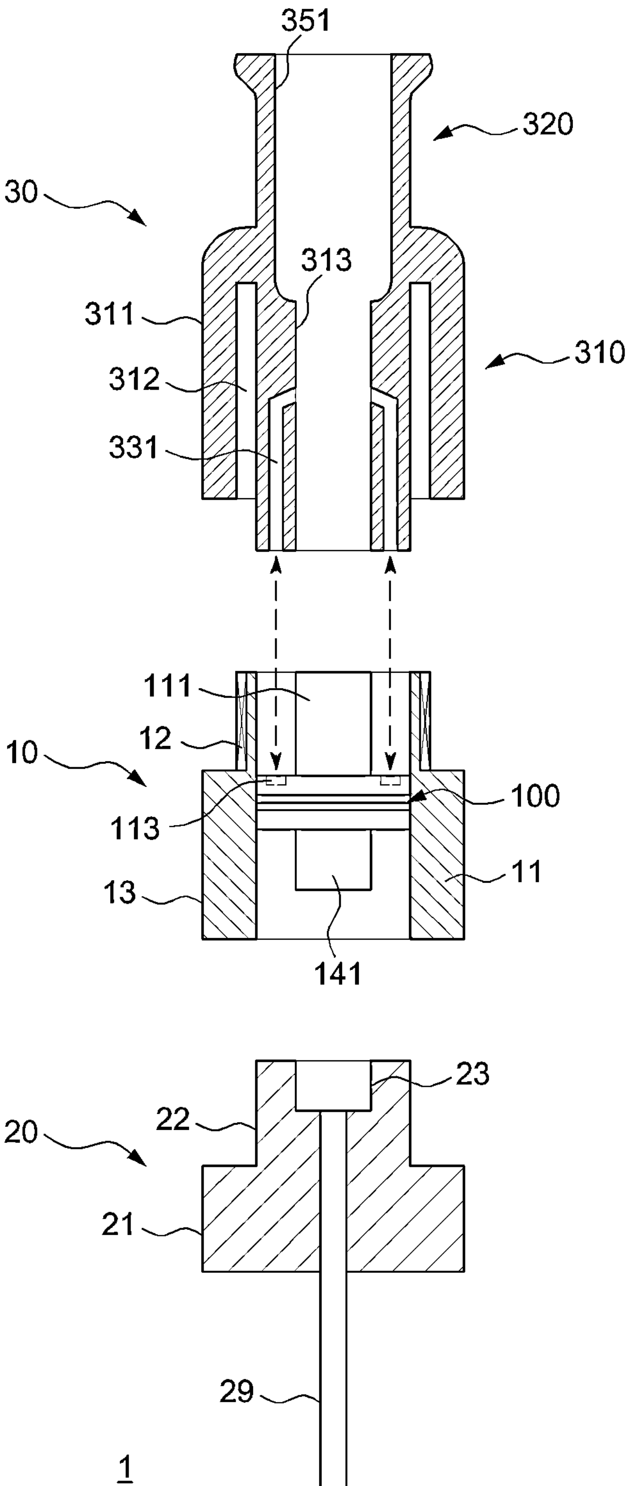
FIG. 2 is an exploded cross-sectional view of the medical needle unit 1 with an air filter part for preventing air injection of FIG. 1.

FIG. 1 is a side view of a medical needle unit 1 with an air filter part for preventing air injection according to an embodiment of the present disclosure, and FIG. 2 is an exploded cross-sectional view of the medical needle unit 1 with an air filter part for preventing air injection of FIG. 1.

As shown in FIGS. 1 and 2, a medical needle unit 1 with an air filter part for preventing air injection (hereafter, "medical needle unit 1") according to an embodiment of the present disclosure may include: a filter part 10 having a built-in filter unit 100 for preventing air injection; a medical needle part 20 coupled to an end of the air filter part 10; and a medicine injection part 30 and 30' coupled to an end of the air filter part 10 opposite to the end to which the medical needle part 20 is coupled to couple an external medicine injector.

The air filter part 10 may include a filter supporting tube 11 having a through-hole formed through the center axis therein, and the filter unit 100 disposed in the filter supporting tube 11.

The filter supporting tube 11 may include a first air filter part coupler tube 12 that is an end facing the medical needle part 20 and is inserted in the medical needle part 20 and a second air filter part coupler tube 13 that is an end facing the medicine injection part 30 and 30' and is coupled to the medicine injection part 30 and 30'.

The first air filter part coupler tube 12 may have an outer diameter for insertion in a first medicine injection part coupler 312 of the medicine injection part 30 and 30', and an inner diameter for inserting a medicine injection tube 313 of the medicine injection part 30 and 30' into the first air filter part coupler tube 12. The first air filter part coupler tube 12 may be coupled to the first medicine injection part coupler 312 in a forced fitting manner. Alternatively, the first air filter part coupler tube 12 may be thread-fastened to the first medicine injection part coupler 312. In this case, a male thread may be formed on the outer surface of the first air filter part coupler tube 12 and a female thread may be formed on the inner surface of the first medicine injection part coupler 312.

The second air filter part coupler tube 13 may have an inner diameter for inserting a medical needle part coupler 22 of the medical needle part 20.

The second air filter part coupler tube 13 may be coupled to the medical needle part coupler 22 in a forced fitting manner. Alternatively, the second air filter part coupler tube 13 may be thread-fastened to the medical needle part coupler 22. In this case, a female thread may be formed on the inner surface of the second air filter part coupler tube 13 and a male thread may be formed on the outer surface of the medical needle part coupler 22.

Figure 3:
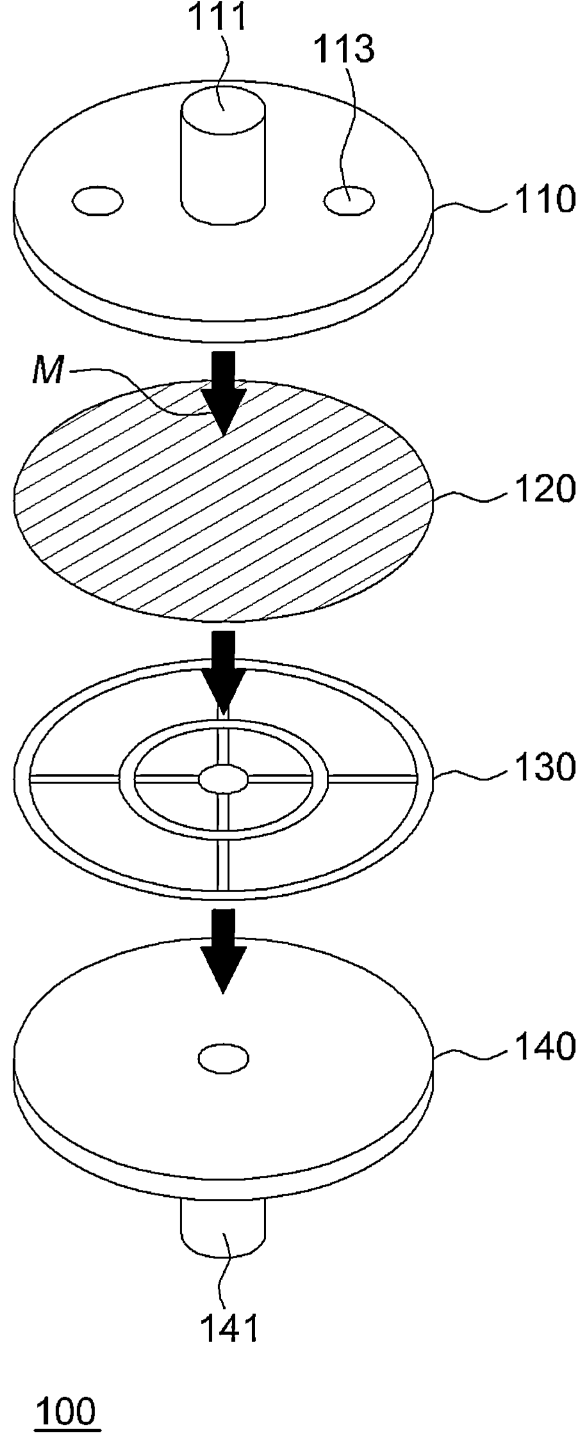
FIG. 3 is an exploded perspective view of a filter unit 100 for preventing air injection.

FIG. 3 is an exploded perspective view of a filter unit 100 for preventing air injection.

As shown in FIG. 3, the filter unit 100 may include a first cover 110 having a medicine injection tube coupler tube 111 on the top thereof, an air injection preventing filter 120, a filter supporter 130, and a second cover 140 having a medicine discharge tube 131 on the bottom thereof such that the air injection preventing filter 120 and the filter supporter 130 are sealed between the first cover 110 and the second cover 140.

The first cover 110 may have a structure that is a plate-shaped structure made of a material which does not transmit air and fluid, has the hollow medicine injection tube coupler tube 111 protruding on the top, and has one or more air filter part medicine injection holes 130 formed on the top around the medicine injection tube coupler tube 111.

The air injection preventing filter 120 may be a hydrophilic membrane of polyvinylidene fluoride (PVDF) or polytetrafluoroethylene (PTFE), a hydrophobic membrane of polytetrafluoroethylene, a polyethersulfone (PES) membrane, a mixed cellulose ester (MCE) membrane, a cellulose acetate (CA) membrane, a nylon membrane, a surfactant free cellulose acetate (SFCA) membrane, or glass fiber.

The air injection preventing filter 120 may be manufactured to have apertures of 0.1 to 0.45 μm.

The air injection preventing filter 120 may have aseptic or antibiotic membrane having the aperture size.

The air injection preventing filter 120 may be formed in a circular shape, an elliptical shape, or a polygonal shape corresponding to the shape of the inside of the filter supporting tube 11.

In this configuration, the outer diameter, long radius, or the length between diagonal lines of the air injection preventing filter 120 may be 4 to 50 mm, depending on the kinds of needles that are used.

This configuration is described with reference to FIG. 2.

The medical needle part 20 may include: a medical needle 29 that is inserted into an affected area for a ultrasound procedure or operation to inject a medicine for ultrasound treatment; and a medical needle holder 21 through which a second end of the medical needle 29 is inserted and fixed and that has the medical needle part coupler 22 coupled to the second air filter part coupler tube 13 of the air filter part 10.

The medical needle part coupler 22 may further include, on the surface facing the air filter part 10, a medicine discharge tube coupler 23 recessed and having an inner diameter corresponding to the outer diameter of the medicine discharge tube 141 of the air filter part 10 so that the medicine discharge tube 141 is inserted therein.

The medical needle part coupler 22 may be configured to detachably couple the medical needle holder 21 to the air filter part 10.

The medical needle part coupler 22 may be coupled to the second air filter part coupler tube 13 in a forced fitting manner. Alternatively, the medical needle part coupler 22 may be thread-fastened to the second air filter part coupler tube 13. In this case, a male thread may be formed on the outer surface of the medical needle part coupler 22 and a female thread may be formed on the inner surface of the second air filter part coupler tube 13.

An end of the medical needle 29 is exposed through the bottom of the medicine discharge tube coupler 23 and communicate with the medicine discharge tube 141 so that medicine can be supplied.

The medical injection part 30 and 30' may include an air filter part coupler 310 to which the air filter part 10 is coupled, and an external medicine injector coupler 320 extending from the air filter part coupler 310 to the medicine injection part 30 and 30' so that an external medicine injector is coupled.

The air filter part coupler 310 may include a medicine injection part shell 311, and a medicine injection tube 313 formed in the medicine injection part shell 311 at a predetermined distance from the inner surface of the medicine injection part shell 311 to form a region of a first medicine injection part coupler 312.

The first air filter part coupler tube 12 is injected in the first medicine injection part coupler 312 and the medicine injection tube 313 is inserted in the first air filter part coupler tube 12, whereby the air filter part and the medicine injection part 30 and 30' are coupled. To this end, the first air filter part coupler tube 12 may have an outer diameter corresponding to the inner diameter of the first medicine injection part coupler 312 and an inner diameter corresponding to the outer diameter of the medicine Injection tube 313.

The connection portions of the medicine injection part shell 311 and the external medicine injector coupler 320 of the medicine injection tube 313 may be integrally connected.

The first air filter part coupler tube 12 may be coupled to the first medicine injection part coupler 312 in a forced fitting manner.

Alternatively, the first air filter part coupler tube 12 may be thread-fastened to the first medicine injection part coupler 312. In this case, a female thread may be formed on the inner surface of the first medicine injection part coupler 312 and a male thread may be formed on the outer surface of the first air filter part coupler tube 12.

A medicine injection tube medicine channel 331 may be formed in the inner wall of the medicine injection tube 313. A medicine that is supplied through the medicine channel 331 of the above configuration is supplied to an air filter part medicine injection hole 113 of the air filter unit 100 for preventing air injection in the early stage of medicine injection, thereby wetting the air injection preventing filter 12 for preventing air injection. Accordingly, air in the air injection preventing filter 120 is prevented in advance from being injected into the medical needle 29.

The external medicine injector coupler 320 may be formed in a tube shape where an external medicine injector is fitted on or inserted in the external medicine injector coupler 320 in a forced medicine fitting manner. In FIG. 1, a second medicine injection part coupler 351 is formed on the inner surface of the external medicine injector coupler 320 and an external medicine injector is inserted in the second medicine injection part coupler 351, but the present disclosure is not limited thereto.

The external medicine injector coupler 320 may be formed in a tube shape to which an external medicine injector is thread-fastened. In this case, a female thread or a male thread may be formed on the inner surface or the outer surface of the external medicine injector coupler 320.

Figure 4:
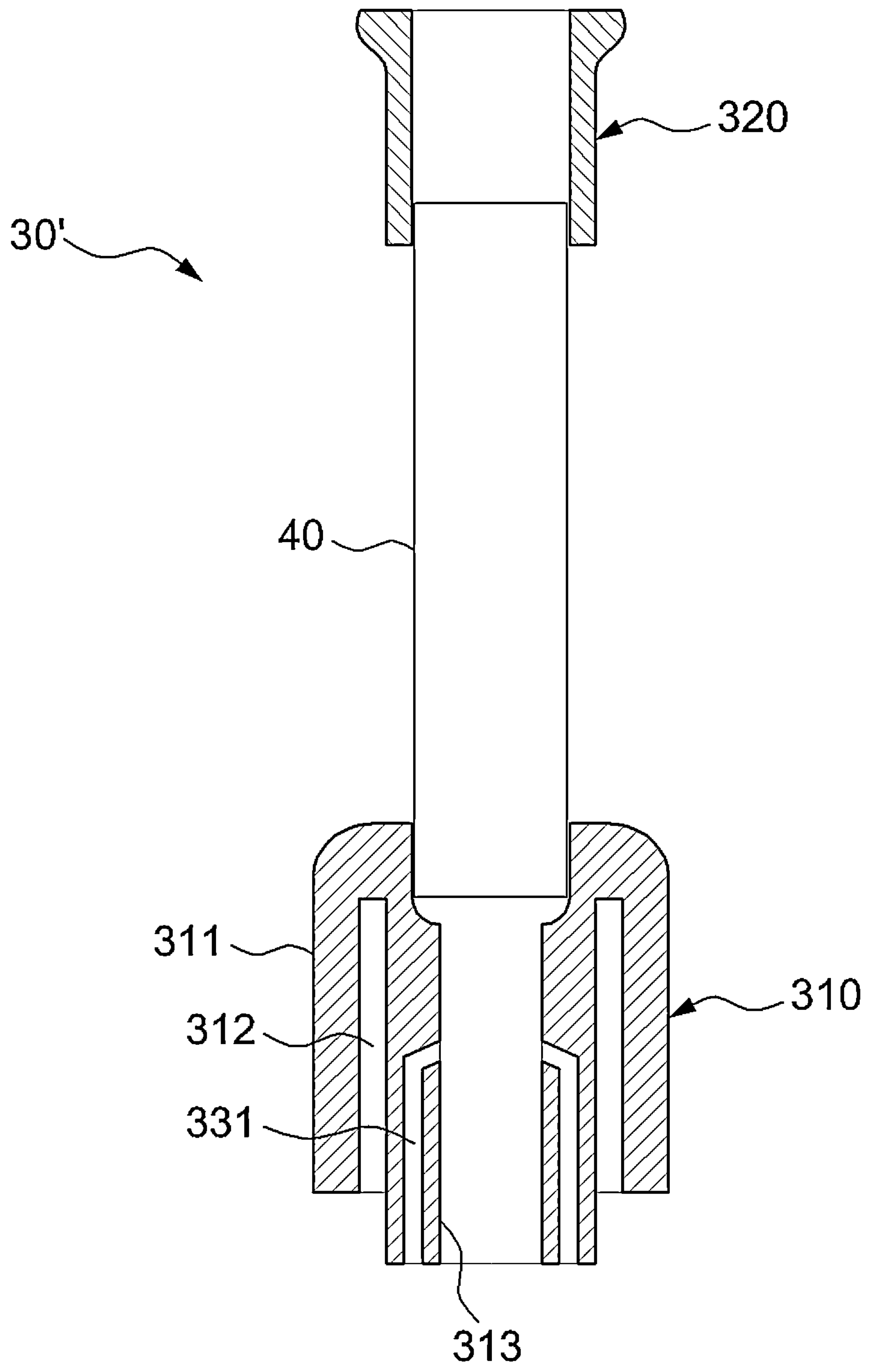
FIG. 4 is a cross-sectional view of a medicine injection part 30' according to another embodiment of the present disclosure.

FIG. 4 is a cross-sectional view of a medicine injection part 30' according to another embodiment of the present disclosure.

As in FIG. 4, the medicine injection part may be a medicine injection part 30' in which the air filter part coupler 310 and the external medicine injector coupler 320 are separated and that further includes an extension tube 40 connecting the air filter part coupler 310 and the external medicine injector coupler 320. By this configuration, the medicine injection part 30' can perform ultrasound treatment regardless of a length.

The air filter part coupler 310, the external medicine injector coupler 320, and the extension tube 40 may be coupled in a forced fitting manner. Alternatively, female threads or male threads may be formed at the joints of the air filter part coupler 310, the external medicine injector coupler 320, and the extension tube 40 to thread-fasten them.

Figure 5:
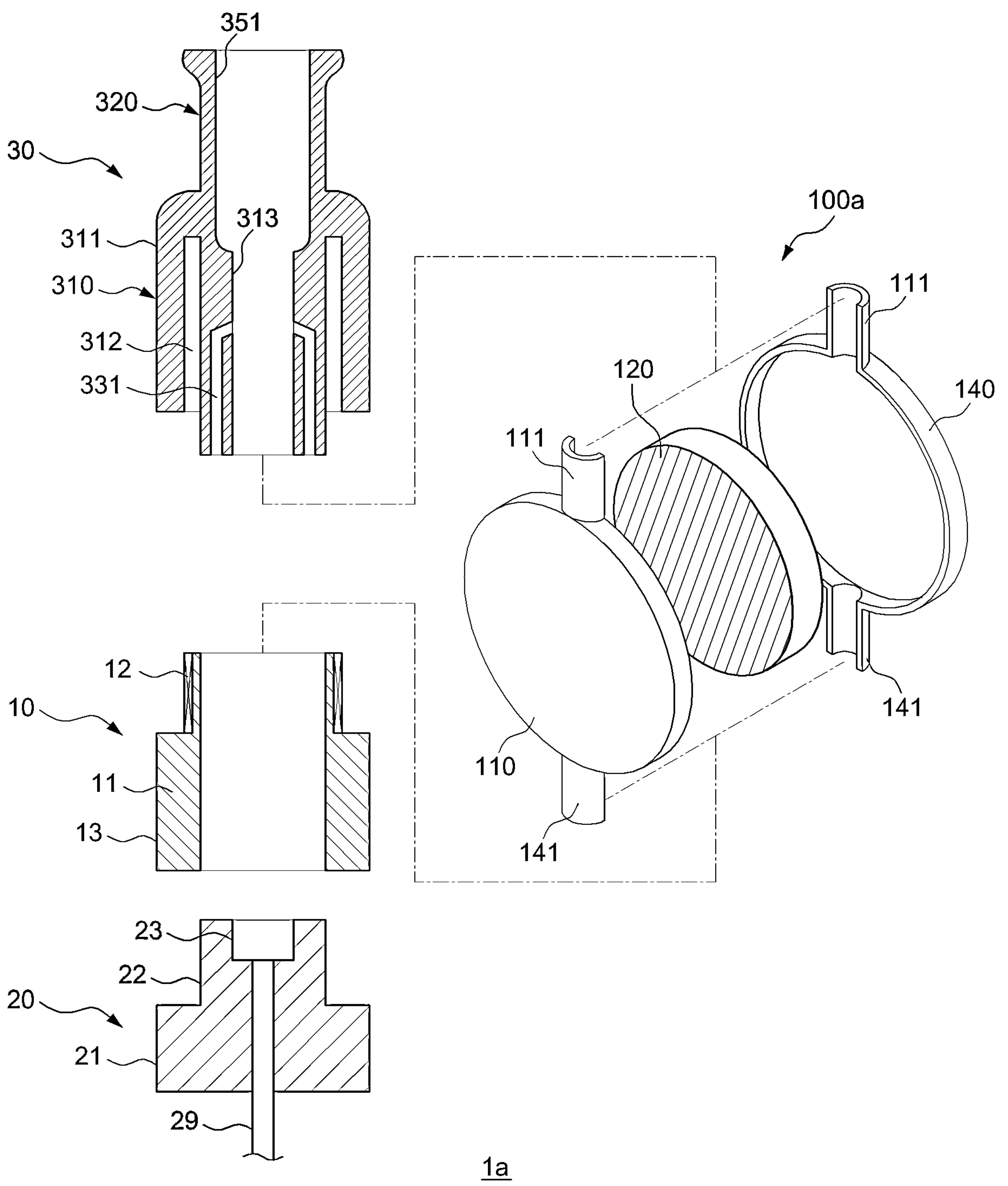
FIG. 5 is an exploded cross-sectional view of a medical needle unit 1*a* with an air filter part for preventing air injection according to another embodiment of the present disclosure.

FIG. 5 is an exploded cross-sectional view of a medical needle unit 1*a* with an air filter part for preventing air injection according to another embodiment of the present disclosure.

As in FIG. 5, the medical needle unit 1*a* may include an air filter part 10, a filter unit 100*a* coupled to the air filter part 10, a medicine injection part 30 and 30' coupled to an end of the filter unit 100*a* that is opposite to the end to which the air filter part 10 is coupled, and a medical needle part 20 coupled to the other end of the air filter part 10 that is different from the end to which the filter unit 100*a* is coupled.

That is, as in FIG. 5, the filter unit 100 of FIGS. 1 to 3 may be configured as the filter unit 100*a* exposed out of the air filter part 10.

In this case, the filter unit 100*a* may include a first cover 110 forming a divided left cover of a laterally laid filter case, a second cover 140 forming a right cover, and an air injection preventing filter 120 laterally laid and positioned between the first cover 110 and the second cover 140.

The filter unit 100*a* having this configuration is positioned at the joint between the air filter part 10 and the medicine injection part 30 and 30', the medicine injection tube coupler tube 111 is coupled to the medicine injection tube 313 of the medicine injection part 30 and 30', and the medicine discharge tube 141 is coupled to the first air filter part coupler tube 12 of the air filter part 10, thereby forming the needle unit 1*a*.

Further, the medicine injection part 30 and 30' may be a medicine injection part 30' having the extension tube 40 of FIG. 4.

Further, the filter unit 100*a* may further include a filter supporter 130 (see FIG. 3) positioned at one or more of the left or right of the air injection preventing filter 120.

Figure 6:
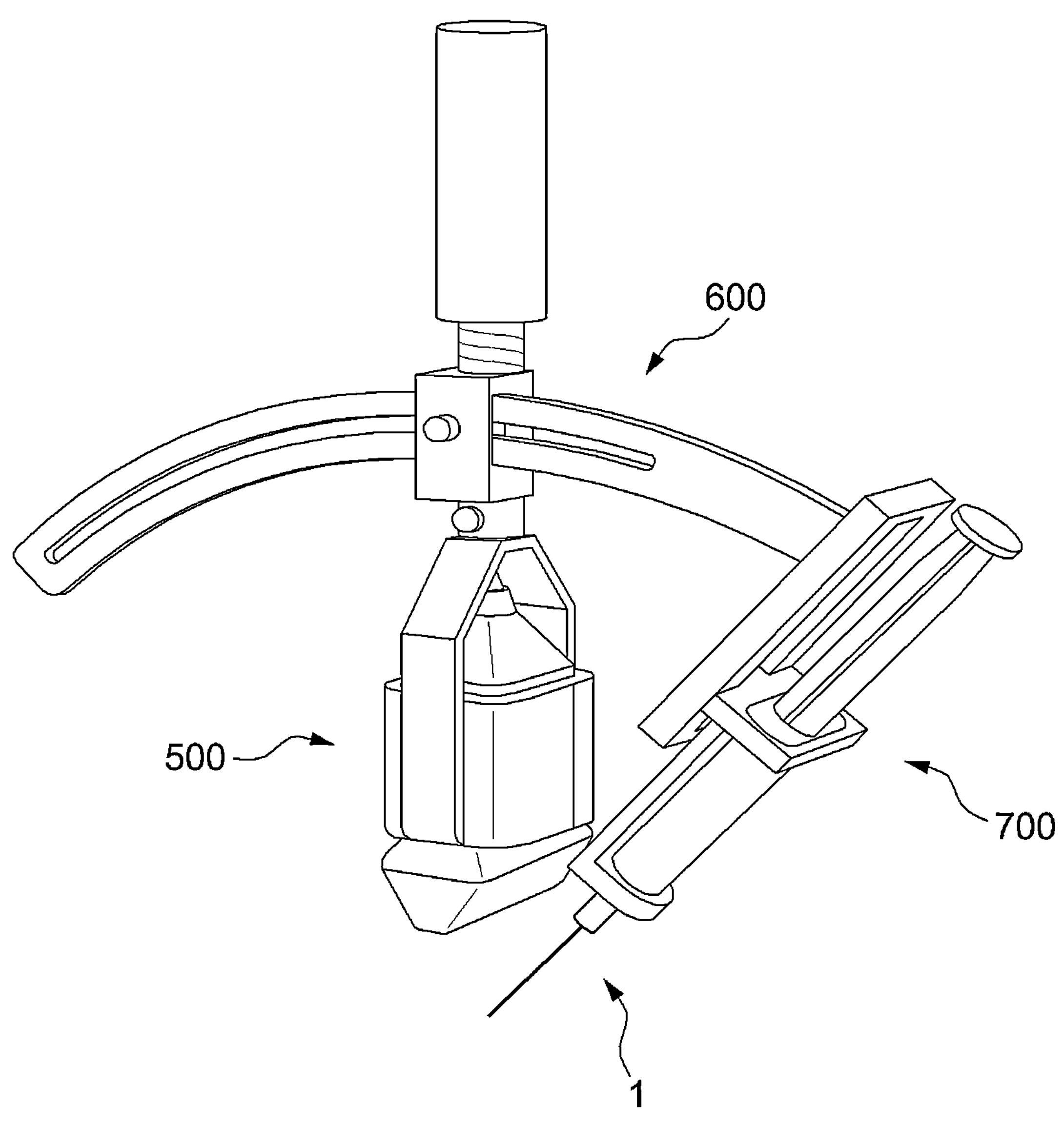
FIG. 6 is a view showing a use state of the medical needle unit 1 according to an embodiment of the present disclosure.

FIG. 6 is a view showing a use state of the medical needle unit 1 according to an embodiment of the present disclosure.

As in FIG. 6, the medical needle unit 1 having the configuration of FIGS. 1 to 4 of an embodiment of the present disclosure may be coupled to an injection unit 700 of an ultrasound treatment device including a ultrasound probe 500, an injection unit support 600, and the injection unit 700 and may be used to inject an injection medicine for a ultrasound procedure or operation into an affected area while preventing air injection.

Figure 7:
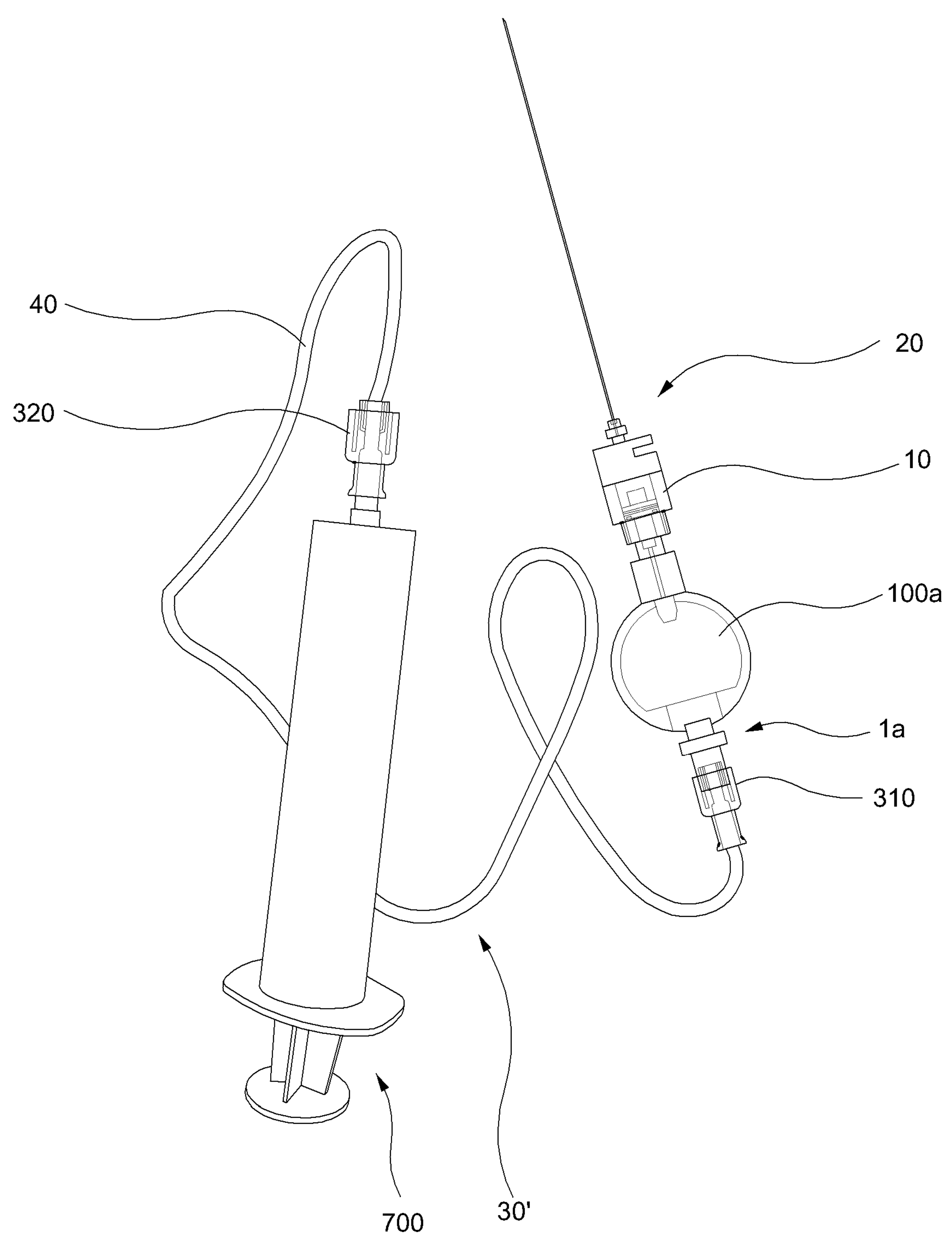
FIG. 7 is a view showing another use state of the medical needle unit 1 according to an embodiment of the present disclosure.

FIG. 7 is a view showing another use state of the medical needle unit 1*a* according to an embodiment of the present disclosure.

As in FIG. 7, the medical needle unit 1*a* may be coupled to the injection unit 700, which is independently used, by extending the air filter part coupler 310 and the external medicine injector coupler 320 through an extension tube 40, connecting the filter unit 100*a* to the air filter part coupler 310, and then connecting the air filter part 10 to the filter unit 100*a*.

In the configuration described above, the couplers of the air filter part 10, the medical needle part 20, the filter unit 100*a*, and the medicine injection part 30 and 30' may be manufactured in various sizes or a standard size to use various syringe units for injecting various medicines that are used in ultrasound treatment.

While the technical spirit of the present disclosure was described in detail through embodiments, it should be noted that the embodiments is for describing, not limiting, the present disclosure. Further, it should be noted that the present disclosure may be achieved in various ways by those skilled in the art without departing from the scope of the present disclosure. Therefore, the technical protective region of the present disclosure should be determined by the scope described in claims.

An embodiment of the present disclosure described above provides an effect of remarkably improving convenience in ultrasound procedures or operations by integrally mounting an air filter part that prevents air injection at a medical needle unit that injects a medicine for taking ultrasound images for ultrasound procedures or operations.

Further, an embodiment of the present disclosure described above provides an effect of enabling ultrasound procedures or operations to be quickly, accurately, and safely performed by preventing qualitative deterioration of ultrasound images by integrally mounting an air filter part that prevents air injection at a needle that injects a medicine for taking ultrasound images for ultrasound procedures or operations.

Further, an embodiment of the present disclosure described above provides an effect of decreasing costs by reducing the frequency of ultrasound procedures or operations by preventing qualitative deterioration of ultrasound images by integrally mounting an air filter part that prevents air injection at a medical needle that injects a medicine for taking ultrasound images for ultrasound procedures or operations.

The effects of the present disclosure are not limited thereto and it should be understood that the effects include all effects that can be inferred from the configuration of the present disclosure described in the following specification or claims.

REFERENCE SIGNS LIST

- 1, 1*a*: Needle Unit
- 10: Filter Part
- 11: Filter Supporting Tube
- 12: First Air Filter Part Coupler Tube
- 13: Second Air Filter Part Coupler Tube
- 20: Medical Needle Part
- 21: Medical Needle Holder
- 22: Medle Needle Part Coupler
- 23: Medicine Discharge Tube Coupler
- 29: Medical Needle
- 30: Medicine Injection Part
- 40: Extension Tube
- 100, 100*a*: Filter Unit
- 110: First Cover
- 111: Medicine Injection Tube Coupler Tube
- 113: Air Filter Part Medicine Injection Hole
- 120: Air Injection Preventing Filter
- 130: Filter Supporter
- 140: Second Cover
- 141: Medicine Discharge Tube
- 310: Air Filter Part Coupler
- 311: Medicine Injection Part Shell
- 313: Medicine Injection Tube
- 312: First Medicine Injection Part Coupler
- 331: Medicine Injection Tube Medicine Channel
- 320: External Medicine Injector Coupler
- 351: Second Medicine Injection Part Coupler
- 500: Ultrasound Probe
- 600: Injection Unit Support
- 700: Injection Unit

What is claimed is:

1. A medical needle unit with an air filter part configured to prevent air injection, the medical needle unit comprising:

the air filter part having a built-in filter unit, both the air filter part and the built-in filter unit being configured to prevent the air injection, wherein the air filter part includes a filter supporting tube having a through-hole defined through a center axis therein, and the built-in filter unit disposed in the filter supporting tube, wherein the built-in filter unit includes:

a first cover having a medicine injection tube coupler tube on a top thereof;

an air injection preventing filter;

a filter supporter; and a second cover having a medicine discharge tube on a bottom thereof, and wherein the air injection preventing filter and the filter supporter are sealed between the first cover and the second cover;

a medical needle part coupled to a first end of the air filter part; and a medicine injection part coupled to a second end of the air filter part opposite to the first end to which the medical needle part is coupled, to be connected to an external medicine injector.

2. The medical needle unit of claim 1, wherein the filter supporting tube includes:

a first air filter part coupler tube that is at an end facing the medicine injection part and is configured to be coupled to the medicine injection part; and a second air filter part coupler tube that is at an end facing the medical needle part and is configured to be inserted in the medical needle part.

3. The medical needle unit of claim 2, wherein the first air filter part coupler tube has an outer diameter for being inserted in a first medicine injection unit coupler of the medicine injection part, and an inner diameter for inserting a medicine injection tube of the medicine injection part into the first air filter part coupler tube.

4. The medical needle unit of claim 2, wherein the second air filter part coupler tube has an inner diameter for inserting a medical needle part coupler of the medical needle part.

5. The medical needle unit of claim 1, wherein the air injection preventing filter has apertures of 0.1 to 0.45 μm.

6. The medical needle unit of claim 1, wherein a length of any one of an outer diameter, a long radius, or a diagonal line of the air injection preventing filter is in a range of 4 to 50 mm.

7. The medical needle unit of claim 1, wherein the medical needle part includes:

a medical needle that is configured to be inserted into an affected area for an ultrasound procedure or operation to inject a medicine for ultrasound treatment; and a medical needle holder through which another end of the medical needle is inserted and fixed and that has a medical needle part coupler coupled to a second air filter part coupler tube of the air filter part.

8. The medical needle unit of claim 7, wherein the medical needle part coupler further includes, on a surface facing the air filter part, a medicine discharge tube coupler recessed and having an inner diameter corresponding to an outer diameter of the medicine discharge tube of the air filter part so that the medicine discharge tube is inserted therein.

9. The medical needle unit of claim 7, wherein the medical needle part coupler is configured to detachably couple the medical needle holder to the air filter part.

10. The medical needle unit of claim 1, wherein the medicine injection part includes:

an air filter part coupler to which the air filter part is coupled; and an external medicine injector coupler extending from the air filter part coupler to the medicine injection part so that the external medicine injector is coupled.

11. The medical needle unit of claim 10, wherein the air filter part coupler includes:

a medicine injection part shell; and a medicine injection tube formed in the medicine injection part shell at a predetermined distance from an inner surface of the medicine injection part shell to form a region of a first medicine injection part coupler.

12. The medical needle unit of claim 10, wherein the medicine injection part is configured such that the air filter part coupler and the external medicine injector coupler are separated, and further includes an extension tube connecting the air filter part coupler and the external medicine injector coupler.

13. A medical needle unit with an air filter part configured to prevent air injection, the medical needle unit comprising:

the air filter part, wherein the air filter part includes:

a filter supporting tube having a through-hole defined through a center axis therein; and a filter unit disposed in the filter supporting tube;

the filter unit coupled to the air filter part, wherein the filter unit includes:

a first cover having a medicine injection tube coupler tube on a top thereof;

an air injection preventing filter:

a filter supporter; and a second cover having a medicine discharge tube on a bottom thereof, and wherein the air injection preventing filter and the filter supporter are sealed between the first cover and the second cover;

a medicine injection part coupled to an end of the filter unit that is opposite to an end to which the air filter part is coupled; and a medical needle part coupled to another end of the air filter part that is different from an end to which the filter unit is coupled.

14. A medical needle unit with an air filter part configured to prevent air injection, the medical needle unit comprising:

the air filter part having a built-in filter unit, both the air filter part and the built-in filter unit being configured to prevent the air injection;

a medical needle part coupled to a first end of the air filter part, wherein the medical needle part includes:

a medical needle that is configured to be inserted into an affected area for an ultrasound procedure or operation to inject a medicine for ultrasound treatment; and a medical needle holder through which another end of the medical needle is inserted and fixed and that has a medical needle part coupler coupled to a second air filter part coupler tube of the air filter part, and wherein the medical needle part coupler further includes, on a surface facing the air filter part, a medicine discharge tube coupler recessed and having an inner diameter corresponding to an outer diameter of a medicine discharge tube of the air filter part so that the medicine discharge tube is inserted therein; and a medicine injection part coupled to a second end of the air filter part opposite to the first end to which the medical needle part is coupled, to be connected to an external medicine injector.

* * * * *